(12) United States Patent
Zeng et al.

(10) Patent No.: US 10,722,316 B2
(45) Date of Patent: Jul. 28, 2020

(54) BIOPROSTHETIC HEART VALVES HAVING ADAPTIVE SEALS TO MINIMIZE PARAVALVULAR LEAKAGE

(71) Applicant: Edwards Lifesciences Corporation, Irvine, CA (US)

(72) Inventors: Qinggang Zeng, Mission Viejo, CA (US); Chacphet Limsakoune, Corona, CA (US); Diana E. Ko, Irvine, CA (US); Christina M. Aguila, Foothill Ranch, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 114 days.

(21) Appl. No.: 15/792,441

(22) Filed: Oct. 24, 2017

(65) Prior Publication Data

US 2018/0042690 A1    Feb. 15, 2018

Related U.S. Application Data

(63) Continuation of application No. 14/533,922, filed on Nov. 5, 2014, now abandoned.
(Continued)

(51) Int. Cl.
*A61F 2/24* (2006.01)
*A61B 50/30* (2016.01)
(Continued)

(52) U.S. Cl.
CPC ............ *A61B 50/30* (2016.02); *A61F 2/0095* (2013.01); *A61F 2/2412* (2013.01);
(Continued)

(58) Field of Classification Search
CPC ..................................... A61F 2/82; A61F 2/24
See application file for complete search history.

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0125393 A1 | 11/1984 |
| EP | 0143246 A2 | 6/1985 |

(Continued)

OTHER PUBLICATIONS

Diew Saijun, et al., "Water Absorption and Mechanical Properties of Water-Swellable Natural Rubber," Songklanakarin J. Sci. Technol., 31 (5), pp. 561-565, Sep.-Oct. 2009.
(Continued)

*Primary Examiner* — Matthew W Schall
(74) *Attorney, Agent, or Firm* — Darren Franklin; Michelle Kim; Sheppard Mullin Richter & Hampton LLP

(57) ABSTRACT

A packaged bioprosthetic heart valve comprising a bioprosthetic heart valve, an adaptive seal and a package. The bioprosthetic heart valve comprises an at least partially dehydrated biological tissue leaflet structure coupled to a supporting frame. The bioprosthetic heart valve has a periphery, an inflow portion, and an outflow portion. The adaptive seal is coupled to the bioprosthetic heart valve around at least a portion of the periphery. The adaptive seal comprises an expandable material that expands after exposure to an initiating condition. The bioprosthetic heart valve and the adaptive seal is stored and contained within the package, which does not contain a liquid storage solution in contact with the bioprosthetic heart valve and the adaptive seal.

14 Claims, 10 Drawing Sheets

Related U.S. Application Data

(60) Provisional application No. 61/900,827, filed on Nov. 6, 2013.

(51) Int. Cl.
*A61F 2/00* (2006.01)
*A61B 50/00* (2016.01)
*A61B 50/33* (2016.01)

(52) U.S. Cl.
CPC ............ *A61F 2/2415* (2013.01); *A61B 50/33* (2016.02); *A61B 2050/002* (2016.02); *A61F 2/2418* (2013.01); *A61F 2250/0069* (2013.01)

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,663 A | 8/1996 | Cottone, Jr. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |

(56) References Cited

U.S. PATENT DOCUMENTS

| | | |
|---|---|---|
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,220,274 B1 | 5/2007 | Quinn |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,998,151 B2 | 8/2011 | St. Goar et al. |
| 8,142,497 B2 | 3/2012 | Friedman |
| 8,517,027 B2 | 8/2013 | Haig |
| 8,839,957 B2 | 9/2014 | Murad et al. |
| 2001/0004715 A1 | 6/2001 | Duran et al. |
| 2001/0023372 A1 | 9/2001 | Chen et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0100920 A1 | 5/2003 | Akin et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0217415 A1 | 11/2003 | Crouch et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0199401 A1 | 9/2005 | Patel et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |

(56) References Cited

U.S. PATENT DOCUMENTS

| | | |
|---|---|---|
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0088836 A1 | 4/2009 | Bishop et al. |
| 2009/0164005 A1 | 6/2009 | Dove et al. |
| 2009/0192599 A1 | 7/2009 | Lane et al. |
| 2010/0049313 A1 | 2/2010 | Alon et al. |
| 2011/0004299 A1 | 1/2011 | Navia et al. |
| 2011/0214398 A1 | 9/2011 | Liburd et al. |
| 2011/0311493 A1 | 12/2011 | Dove et al. |
| 2012/0290079 A1 | 11/2012 | Murad et al. |
| 2013/0190857 A1 | 7/2013 | Mitra et al. |
| 2013/0197622 A1 | 8/2013 | Mitra et al. |
| 2013/0331929 A1 | 12/2013 | Mitra et al. |
| 2014/0277413 A1 | 9/2014 | Richter et al. |

FOREIGN PATENT DOCUMENTS

| | | |
|---|---|---|
| SU | 116573 A1 | 11/1958 |
| SU | 1697790 A1 | 12/1991 |
| WO | 9213502 A1 | 8/1992 |
| WO | 9742871 A1 | 11/1997 |
| WO | 9843556 A1 | 10/1998 |
| WO | 0141828 A1 | 6/2001 |
| WO | 2008073582 A2 | 6/2008 |
| WO | 2014145564 A2 | 9/2014 |

OTHER PUBLICATIONS

Holger Wack, et al., "Water-Swellable material—Application in Self-Healing Systems," Proceedings of the First International Conference on Self Healing Materials Apr. 18-20, 2007, Noordwijk aan Zee, The Netherlands.

http://en.wikipedia.org/wiki/Expandable_water_toy, Expanadable Water Toy, Accessed on Mar. 29, 2013.

http://www.dermasciences.com/pedf/XtrasorbBrochure2011.pdf, Moist Wound healing Dressing, May 15, 2013.

http://www.scapa.com/files/pages/Scapa_Cable_Solutions_online.pdf, Scapa Cable Solutions Online, May 15, 2013.

Norton, J., et al., "Extremely Water Absorbent Nonwovens Produced with Hyrdophilic Water based Emulsion Polymer".

Omidian H., et al., "Recent Developments in Superporous Hydrogels," J Pharm. Pharmacol., 59 (3), pp. 317-327, 2007.

Philippe Genereux, et al., "Paravalvular Leak After Transcatheter Aortic Valve Replacement: The New Achilles' Heel? A Comprehensive Review of the Literature," J AM Coll Cardiol., vol. 61, No. 11, pp. 1125-1136, 2013.

T. Bussemer, et al., "Evaluation of the Swelling, Hydration and Rupturing Properties of the Swelling Layer of a Rupturable Pulsatile Drug Delivery System," European Journal of Pharmaceutics and Biopharmaceutics 56, pp. 261-270, 2003.

Estler, C.J. et al., "Lehrbuch der allgemeinen und systematischen Pharmakologie und Toxikologie", Schattauer, 1986.

Hof, Herbert et al., "Duale Reihe/ Medizinische Mikrobiologie", George Thieme Verlag, 2000, Ed.3.

Gilbert, Thomas W. et al., "Decellularization of tissues and organs", Biomaterials, vol. 7, Mar. 7, 2006.

Glycerin, http://de.wikipedia.org/wiki/Glycerin.

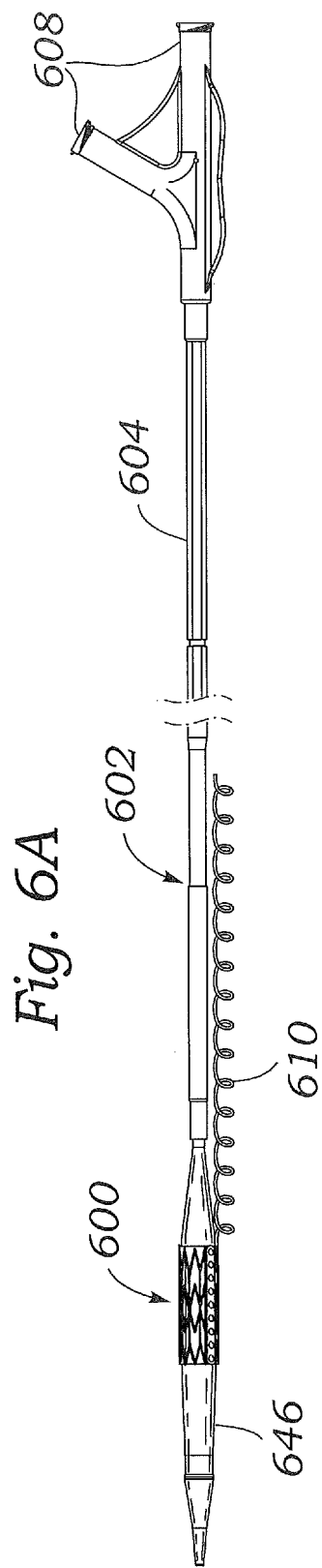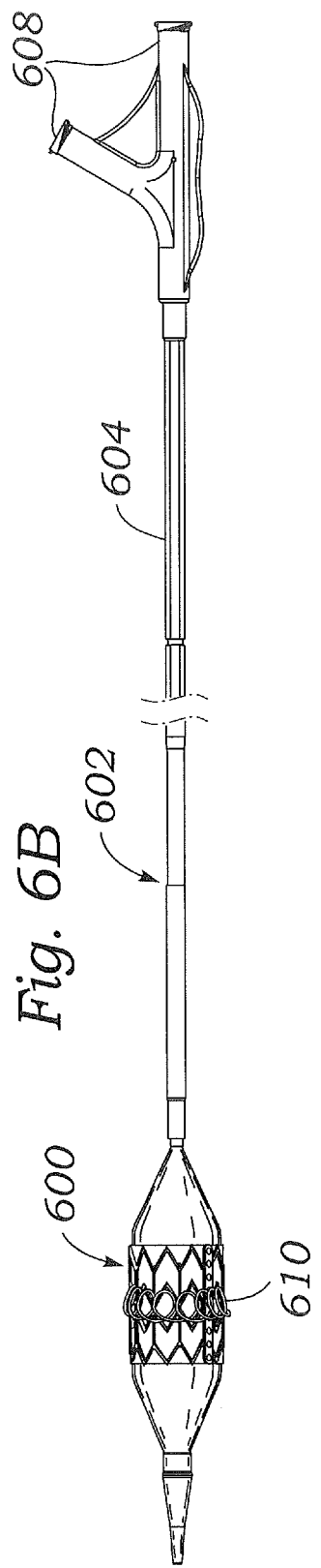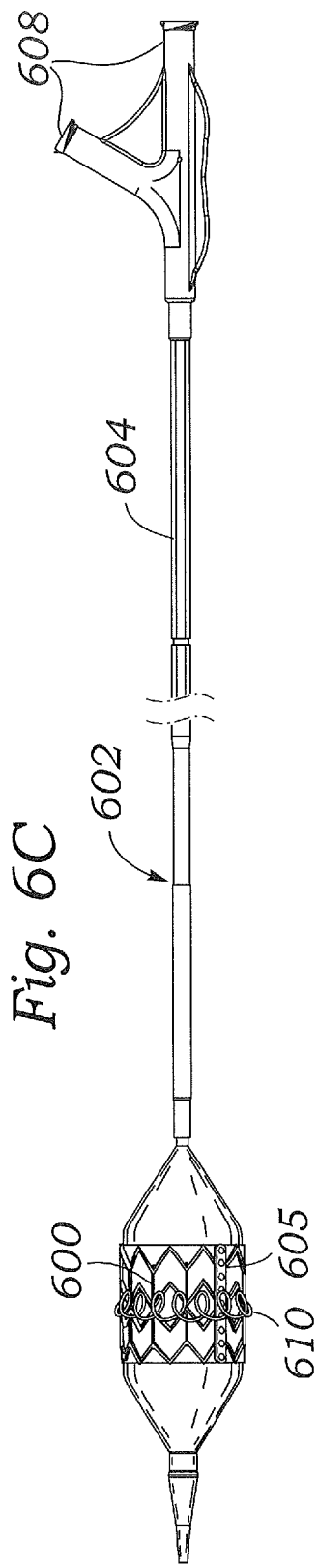

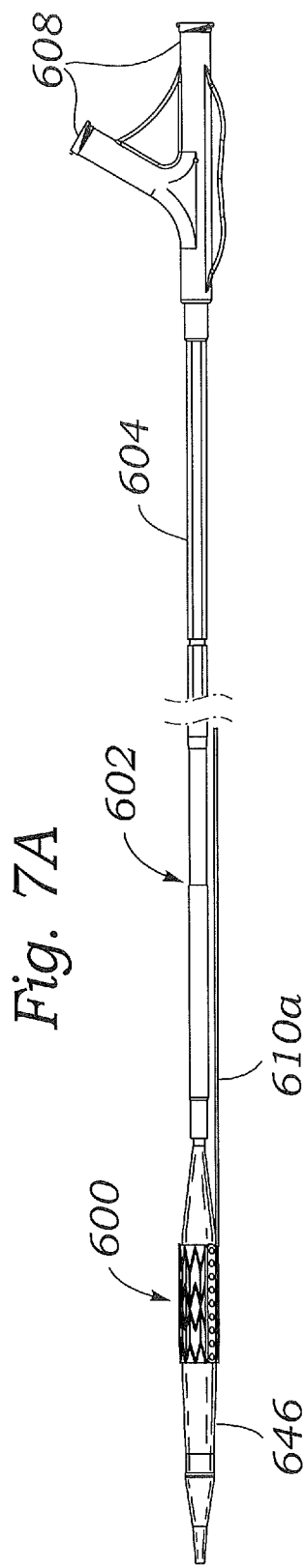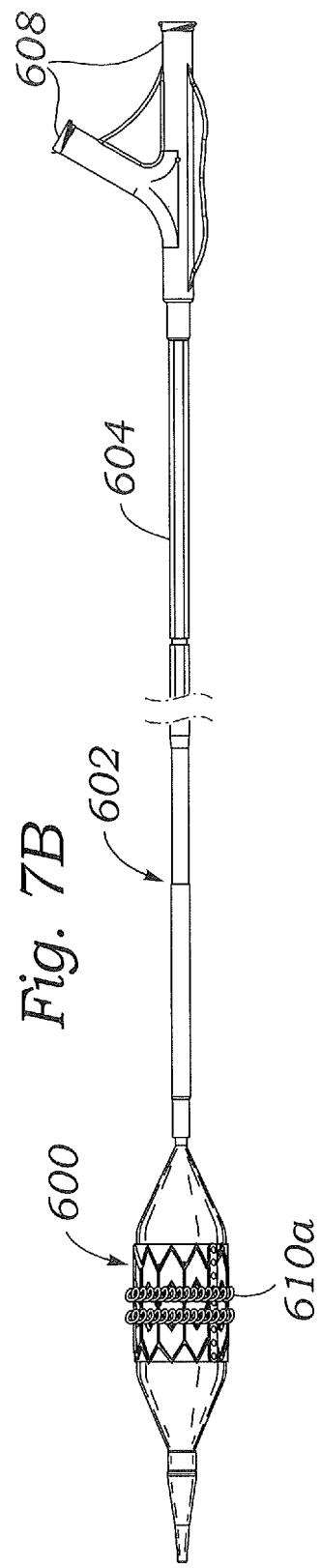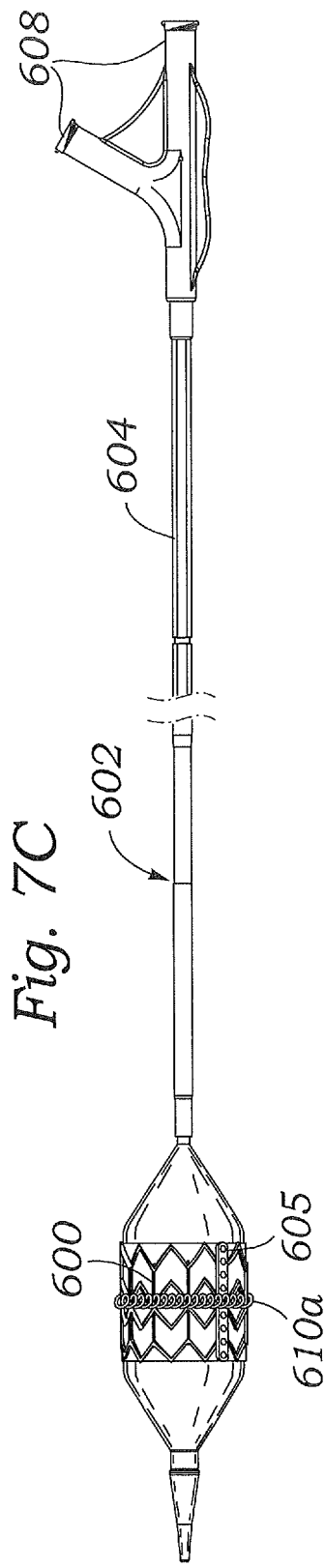

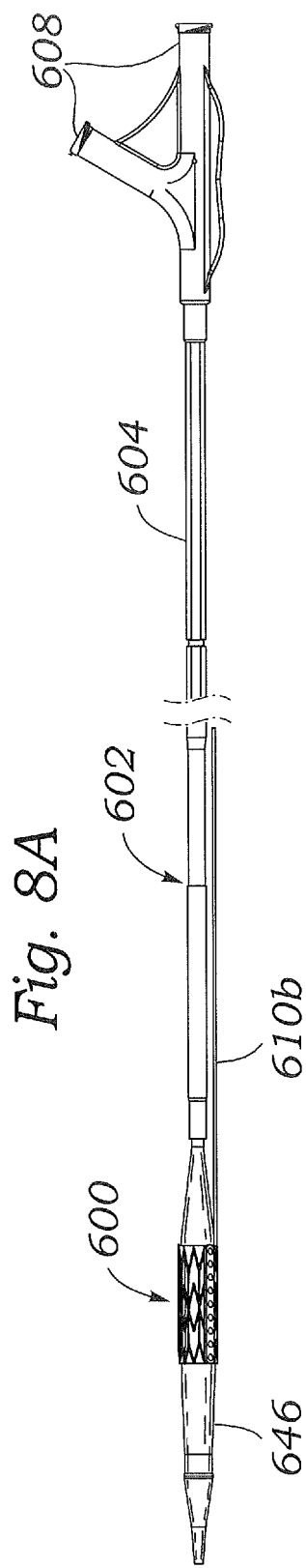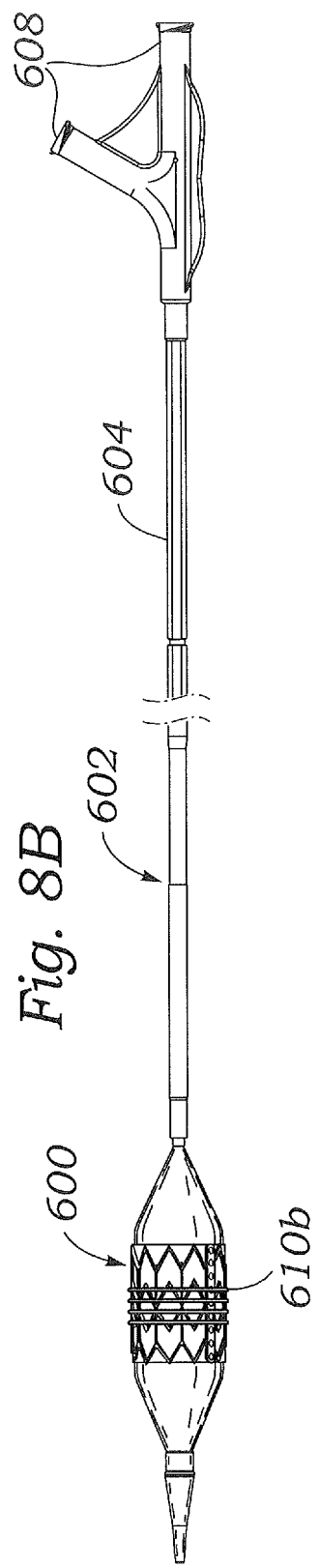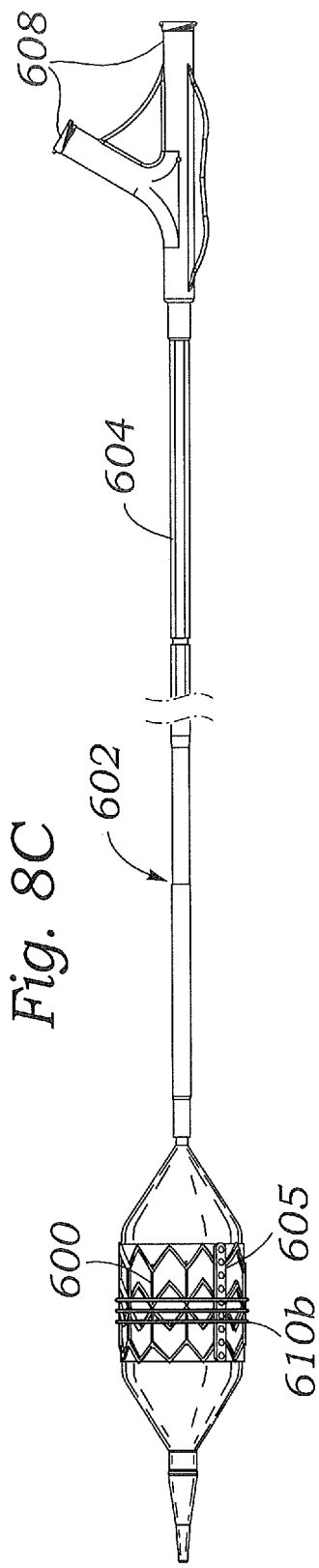

BIOPROSTHETIC HEART VALVES HAVING ADAPTIVE SEALS TO MINIMIZE PARAVALVULAR LEAKAGE

CROSS-REFERENCE TO RELATED APPLICATION

This application is a continuation of U.S. patent application Ser. No. 14/533,922, filed Nov. 5, 2014, which claims the benefit of U.S. Patent Application No. 61/900,827, filed Nov. 6, 2013, the entire disclosures of which are incorporated herein by reference.

FIELD OF THE INVENTION

The invention relates to a heart valve prosthesis and, more particularly, to a heart valve prosthesis having an adaptive seal that minimizes perivalvular leakage following implantation.

BACKGROUND

Perivalvular leakage (PVL) is a complication that is related to the replacement of heart valves. It occurs when blood flows through a channel or gap between the structure of an implanted valve and the cardiac or arterial tissue due to a lack of appropriate sealing.

Intimate apposition of replacement heart valves and the surrounding cardiac or arterial walls seals the valve and minimizes PVL. In certain cases, however, a seal cannot be achieved, leaving irregular gaps of different sizes and shapes between the valve and the cardiac or arterial walls. This may result from inadequate sizing, incomplete expansion of the valve, an irregularly deformed valve, or highly eccentric or irregular calcification pattern on the leaflets or valve annulus.

PVL has been shown to greatly affect the clinical outcome of transcatheter aortic valve replacement procedures, and the severity of perivalvular leakage has been correlated with patient mortality. What is therefore needed is a replacement bioprosthetic heart valve which permits a conforming engagement or fit with the surrounding cardiac or arterial wall so as to substantially fill in the gaps or channels that often result in PVL.

BRIEF SUMMARY

Bioprosthetic heart valves having the adaptive seals described herein are preferably valves which comprise a biological tissue that has been treated so as to not require storage in liquid preservative solutions. While mechanical heart valves are capable of being stored in a dry state, valves having biological tissue typically require storage in liquid preservative solutions. Storage in liquid preservative solutions introduces a host of challenges for valves which include adaptive seals, particularly for those which are activated to expand upon exposure to liquid.

Significant advantages are provided by the bioprosthetic heart valves disclosed herein, in which the biological tissue is treated so as to permit dry storage of the valves without a liquid storage solution. The adaptive seals can be exposed on the heart valve without requiring encapsulation or a barrier from the environment, as would be required if the valves were to be stored in a liquid preservation solution. To that end, the adaptive seals can simply comprise the expandable material exposed or contained within a permeable or semi-permeable material that permits fluid to come into contact with the expandable material, while supporting or containing the expandable material. In a preferred embodiment, the replacement heart valve or the adaptive seal is not selectively encapsulated by a non-permeable barrier.

The simplicity of being able to provide an adaptive seal structure, without selective encapsulation, provides significant advantages over prior art heart valves in which the selective encapsulation of the adaptive seal in a liquid storage solution is a necessity. The selective encapsulation methods of the prior art are required to permit the tissue portion of the valve to be in contact with the liquid storage solution while at the same time segregating the adaptive seal portion from the liquid storage solution. If the adaptive seal is not selectively encapsulated from the liquid storage solution, it will expand and render the heart valve unusable.

The bioprosthetic heart valves contemplated within this disclosure can be any implantable heart valve which preferably comprises a biological tissue. Such valves include transcatheter valves, surgical valves, minimally-invasive valves, and the like. The biological tissue can be derived from animal sources, preferably, from pericardial tissue, and most preferably, from bovine pericardial tissue. The biological tissue is used to form the leaflets of the heart valve and is mounted to a supporting frame or stent to form a bioprosthetic heart valve. Because the valves are stored dry, the biological tissues are treated so as to preserve their pliability and flexibility in a dry state, e.g., without storage in a liquid storage solution.

The terms "dry" or "dehydrated", as used herein, are understood to include residual moisture or humidity from the ambient environment and is intended to mean that the valves are not immersed in, or in contact with, a liquid or a storage solution.

In one embodiment, a method for manufacturing a bioprosthetic heart valve is described. The method comprises providing a bioprosthetic heart valve comprising a biological tissue that has been treated with a treatment solution comprising a polyhydric alcohol, the bioprosthetic heart valve having a periphery, an inflow portion and an outflow portion. The method further comprises coupling an adaptive seal to the bioprosthetic heart valve, the adaptive seal comprising an expandable material that expands after exposure to an initiating condition. The method further comprises packaging the bioprosthetic heart valve and the coupled adaptive seal in a package that does not contain a liquid storage solution in contact with the bioprosthetic heart valve and the coupled adaptive seal. In a preferred embodiment, the adaptive seal is not further encapsulated, segregated or enclosed from the biological tissue.

In accordance with a first aspect of the embodiment, the polyhydric alcohol is glycerol.

In accordance with a second aspect of the embodiment, the biological tissue is at least partially dehydrated following treatment with the treatment solution.

In accordance with a third aspect of the embodiment, the adaptive seal is a hydrophilic polymer or a hydrogel-coated wire.

In accordance with a fourth aspect of the embodiment, the hydrophilic polymer or the hydrogel-coated wire comprises a biodegradable cross-linker. Expansion of the adaptive seal is delayed for a period of time after exposure to the initiating condition.

In accordance with a fifth aspect of the embodiment, the initiating condition is one or more selected from the group consisting of: a change in temperature, a change in the electrical field, a change in the magnetic field, a change in the chemical environment, a change in pH, and contact with a liquid.

In accordance with a sixth aspect of the embodiment, the expandable material expands longitudinally, radially, or both longitudinally and radially relative to the bioprosthetic heart valve after exposure to the initiating condition.

In accordance with a seventh aspect of the embodiment, the bioprosthetic heart valve comprises a stent and the coupling comprises coating the stent with the adaptive seal or coupling patches within open cells defined by the stent.

In another embodiment, a packaged bioprosthetic heart valve is provided. The packaged bioprosthetic heart valve comprises a bioprosthetic heart valve, an adaptive seal coupled to the bioprosthetic heart valve, and a sealed package containing the bioprosthetic heart valve and the adaptive seal. The bioprosthetic heart valve comprises a dehydrated biological tissue leaflet structure coupled to a supporting frame, the bioprosthetic heart valve having a periphery, an inflow portion, and an outflow portion. The adaptive seal comprises an expandable material that expands after exposure to an initiating condition. The sealed package containing the bioprosthetic heart valve and the adaptive seal does not contain a liquid storage solution in contact with the bioprosthetic heart valve and the adaptive seal.

In accordance with a first aspect of the embodiment, the adaptive seal is a hydrophilic polymer or a hydrogel-coated wire.

In accordance with a second aspect of the embodiment, the adaptive seal is a hydrogel comprising a biodegradable cross-linker and expansion of the adaptive seal is delayed for a period of time after exposure to the initiating condition.

In accordance with a third aspect of the embodiment, the adaptive seal is a hydrogel-coated wire comprising a shape memory metal, the hydrogel-coated wire changing from a first configuration to a second configuration upon reaching or exceeding a transformation temperature.

In accordance with a fourth aspect of the embodiment, in the first configuration, the hydrogel-coated wire has one of a straight or a coiled configuration and in the second configuration, the hydrogel-coated wire has the other of the straight or coiled configuration.

In accordance with a fifth aspect of the embodiment, the adaptive seal is coupled to the bioprosthetic heart valve at a spaced distance from both of the inflow and outflow portions.

In accordance with a sixth aspect of the embodiment, the adaptive seal is provided circumferentially about the bioprosthetic heart valve.

In accordance with a seventh aspect of the embodiment, the bioprosthetic heart valve further comprises a sewing ring and the adaptive seal is coupled to and exposed from the sewing ring or contained within the sewing ring.

In accordance with an eighth aspect of the embodiment, the supporting frame is a stent comprising a plurality of struts and open cells.

In accordance with a ninth aspect of the embodiment, the adaptive seal is coupled to one or more struts of the supporting frame.

In accordance with a tenth aspect of the embodiment, the adaptive seal forms one of a coating on at least a portion of the stent.

In accordance with an eleventh aspect of the embodiment, the adaptive seal is provided as patches disposed within the open cells defined by the stent.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which:

FIGS. 6A-6C are broken plan views of an embodiment of an expandable bioprosthetic heart valve and its delivery system in the various stages from a collapsed delivery configuration with the adaptive seal being adjacent the delivery system (FIG. 6A), an intermediate configuration with the adaptive seal is positioned around the bioprosthetic heart valve (FIG. 6B) and an expanded configuration, ready for full expansion of the adaptive seal (FIG. 6C).

FIGS. 7A-7C are broken plan views of another embodiment of an expandable bioprosthetic heart valve and its delivery system in the various stages from a collapsed delivery configuration with the adaptive seal being adjacent the delivery system (FIG. 7A), an intermediate configuration with the adaptive seal is positioned around the bioprosthetic heart valve (FIG. 7B) and an expanded configuration, ready for full expansion of the adaptive seal (FIG. 7C).

FIGS. 8A-8C are broken plan views of an expandable bioprosthetic heart valve and its delivery system in the various stages from a collapsed delivery configuration with the adaptive seal being adjacent the delivery system (FIG. 8A), an intermediate configuration with the adaptive seal is positioned around the bioprosthetic heart valve (FIG. 8B) and an expanded configuration, ready for full expansion of the adaptive seal (FIG. 8C).

Like numerals refer to like parts throughout the several views of the drawings.

DETAILED DESCRIPTION OF THE PREFERRED EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Figure 1A:
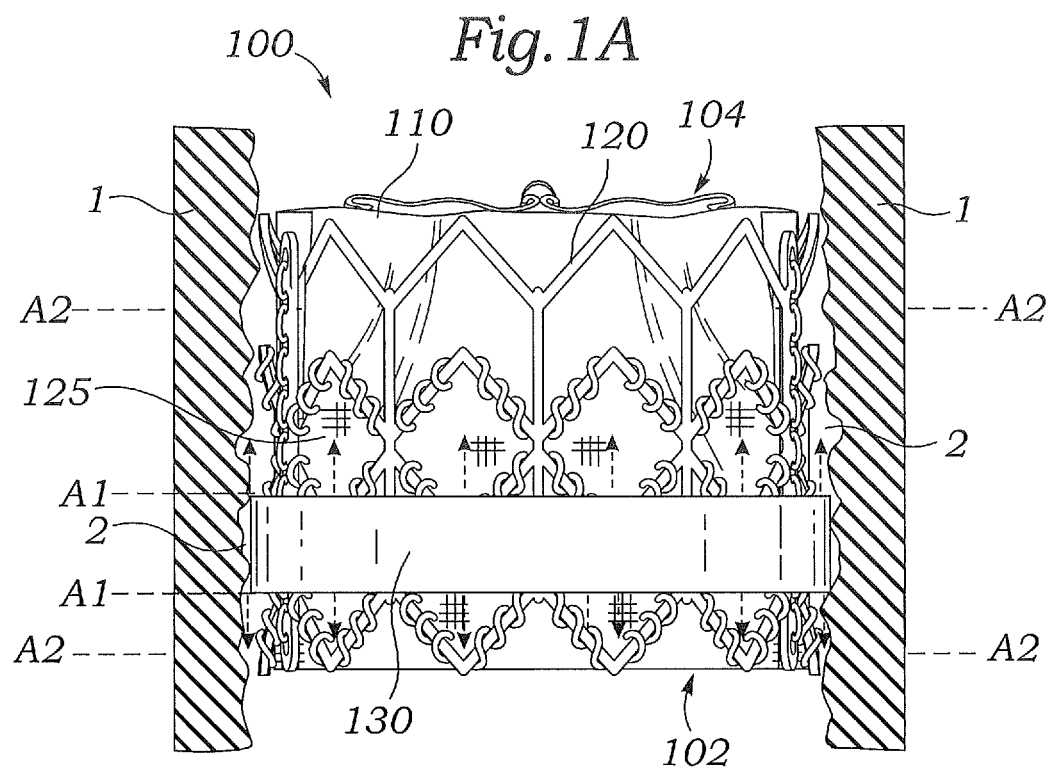
FIG. 1A is a side view of an embodiment of an implanted bioprosthetic heart valve with an adaptive seal in a substantially unexpanded state. The arterial walls are cut away to show the gaps between the implanted bioprosthetic heart valve and the arterial walls.
Figure 1B:
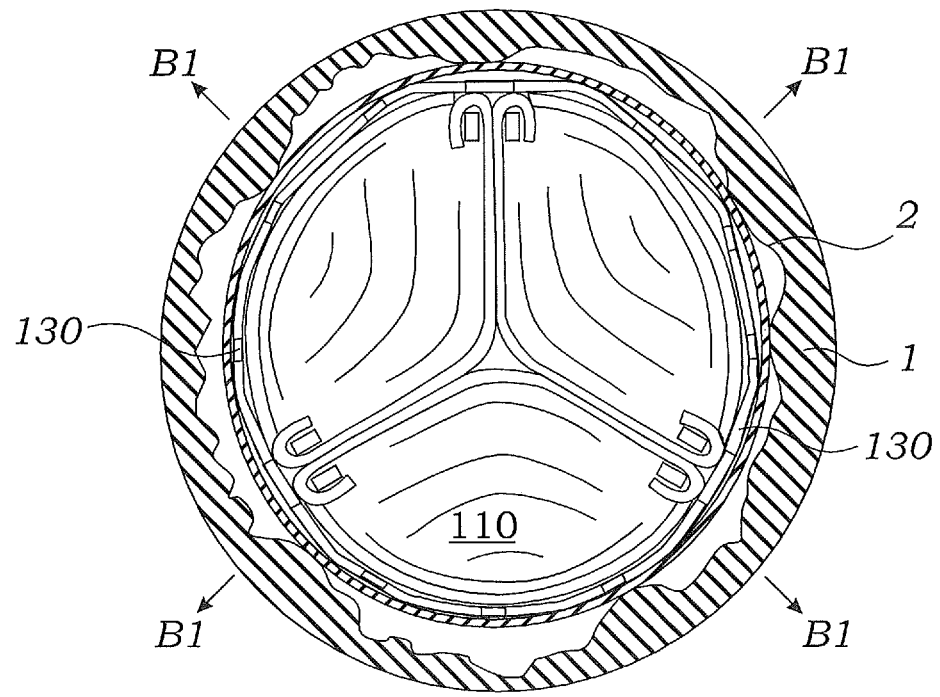
FIG. 1B is a plan view of the outflow portion of the implanted bioprosthetic heart valve of FIG. 1A showing the adaptive seal in a substantially unexpanded state within the arterial walls.

FIGS. 1A and 1B depict a transcatheter heart valve 100 that has been expanded and implanted within an arterial wall 1. The transcatheter heart valve 100 generally comprises a biological tissue leaflet structure 110 that is coupled to an expandable frame or stent 120. It is understood that the stent 120 can either be self-expanding or balloon-expandable. The heart valve 100 further comprises an inflow portion 102, an outflow portion 104 and a skirt 125 that is coupled to the stent 120, preferably by sutures, and located proximate the inflow portion 102.

The external peripheral surface of the heart valve 100 is shown to be in discontinuous engagement with the inner surface of the arterial wall 1 as shown by the gaps or voids 2 between them. These gaps result because the inner surface of the arterial wall 1 is typically an irregular surface. To provide a conforming fit or engagement between the heart valve 100 and the inner surface of the arterial wall 1, an adaptive seal 130 is provided around the external peripheral surface of the heart valve 100. The adaptive seal 130 preferably comprises an expandable or swellable material, such as hydrogels (e.g., zwitterionic hydrogels), super absorbent polymers (SAPs), elastomeric materials or other swellable or absorbent polymer or elastomeric materials. Preferably, the adaptive seal 130 does not comprise silicone or other lubricious materials or polymers that would potentially cause the implanted valve 100 to slip or dislodge from its initial site of implantation.

The adaptive seal 130 can be coupled to the outer periphery of the stent 120, as shown in FIGS. 1A and 1B, by adhesives or by one or more sutures. As can be seen in FIGS. 1-2, the stent 120 further defines a plurality of open spaces or cells. Thus, the adaptive seal 130 can also be provided as a plurality of discrete patches that can be disposed within selected ones of the plurality of open spaces or cells defined by the stent 120.

As shown in FIGS. 1A and 1B, the adaptive seal 130 has a substantially unexpanded length (A1-A1, FIG. 1A) and a substantially unexpanded radial thickness (B1-B1, FIG. 1B) upon initial implantation. Because the adaptive seal 130 will expand both along its length and radial thickness, it is preferably positioned around the heart valve 100 at a sufficient distance away from both the inflow portion 102 and outflow portion 104 such that the fully expanded adaptive seal 130 does not extend beyond the stent 120. In addition, the adaptive seal 130 is constructed such that inward radial expansion into the lumen of the heart valve is limited, if not prevented. Thus, expansion of the adaptive seal 130 is preferably limited to the area between the outer periphery of the stent 120 and the arterial wall 1.

Figure 2A:
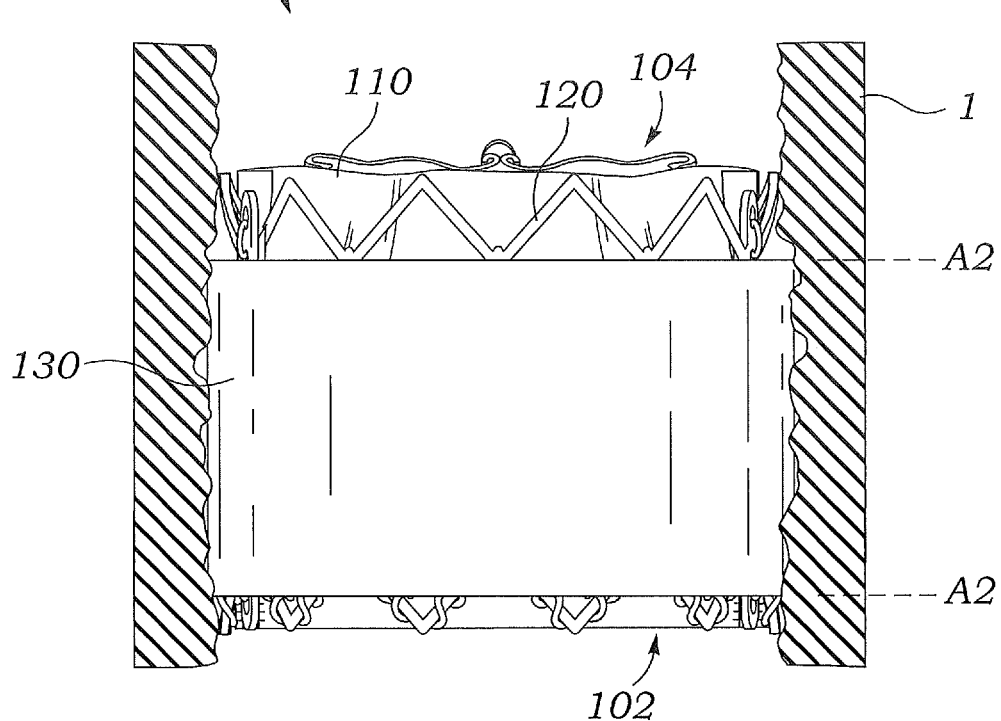
FIG. 2A is a side view of the implanted bioprosthetic heart valve with the adaptive seal in a substantially expanded state. The arterial walls are cut away to show the adaptive seal expanded to fill at least some of the gaps between the implanted bioprosthetic heart valve and the arterial wall.
Figure 2B:
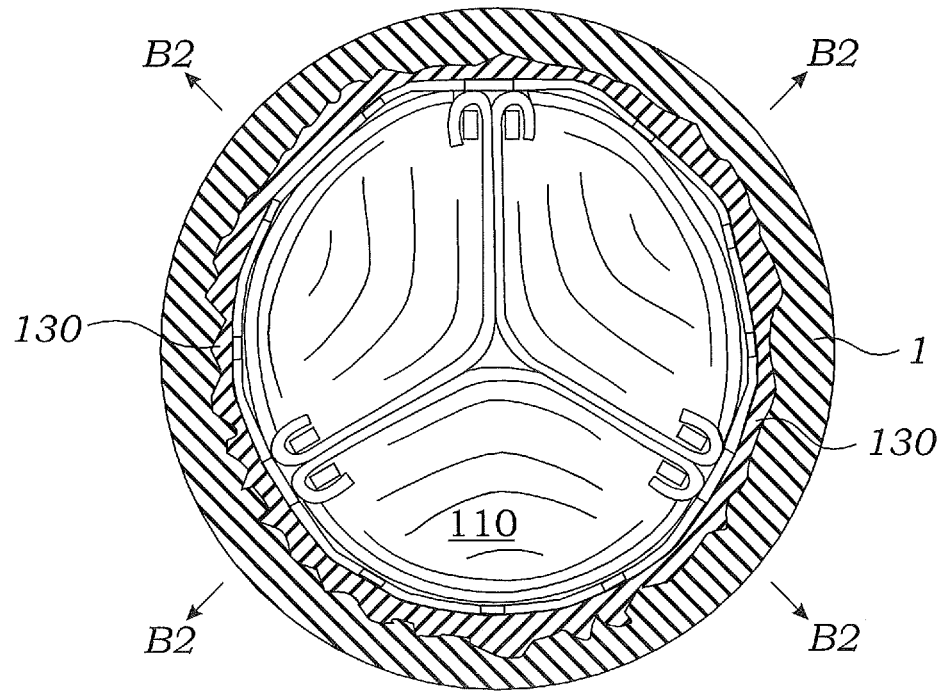
FIG. 2B is a plan view of the outflow portion of the implanted bioprosthetic heart valve showing the adaptive seal in a substantially expanded state, with the arterial walls cut away to reveal the implanted bioprosthetic heart valve.

FIGS. 2A and 2B depict the transcatheter heart valve 100 of FIGS. 1A and 1B in which the adaptive seal 130 has expanded after exposure to an initiating condition. Expansion of the adaptive seal 130 takes place in a conforming, non-rigid manner and the adaptive seal 130 preferably expands in directions of least resistance, e.g., into the spaces or gaps 2 between the stent 120 and the arterial wall 1. In other words, the expansion of the adaptive seal 130 takes place to a greater degree in areas where there are larger gaps between the stent 120 and the arterial wall 1 and to a lesser degree in areas where the gaps 2 are smaller. The adaptive seal 130 preferably expands along one or both of its longitudinal length (A2-A2, FIG. 2A) and its radial thickness (B2-B2, FIG. 2B). In the embodiment depicted herein, the adaptive seal 130 is shown to have not expanded radially inward from the stent 120 and thus will not interfere with the blood flow through the valve 100.

In a preferred embodiment, the adaptive seal 130 comprises a hydrogel material. The hydrogel can be provided as a colloidal gel, such as a hydrocolloid, a coating, a film, or a foam, or it can be provided on a substrate, such as on a cloth or about a shape memory metal or metal coil. While the embodiments depicted in FIGS. 1A and 1B depict the adaptive seal 130 as a strip of material that is affixed to the outer periphery of the stent 120, it is understood that the stent 120 can be directly coated with a hydrogel material. Thus, in one preferred embodiment, the stent 120 is coated or dipped in a hydrogel solution, then allowed to dry before it is coupled to the biological tissue to form a heart valve.

In a preferred embodiment, the adaptive seal 130 comprises a substrate and an expandable material, such as hydrogels, such as zwitterionic hydrogels, SAPs, elastomeric materials or other swellable or absorbent polymer or elastomeric material disposed on the substrate. The substrate can be an impermeable material, such as a film (e.g., a MYLAR® polyester film), or it can be permeable material, such as a densely-woven cloth. In either case, the substrate is expandable, elastically or otherwise, such that it can be wrapped around the external periphery of the heart valve in a collapsed state and expand as the heart valve is deployed to an expanded state. In embodiments where the hydrogel material is disposed on an inelastic material, such as a metal film or coil, the inelastic material assumes a particular geometry (e.g., folded, coiled, etc.) that permits expansion.

Additionally, the substrate is preferably positioned outwardly of the stent 120 and between the stent 120 and the hydrogel material. In the embodiment depicted in FIGS. 1A-1B and 2A-2B, the main function of the substrate is to prevent the hydrogel material from expanding radially inward and thus to limit the expansion of the hydrogel material in a radially outward direction along B2-B2 as depicted in FIG. 2B. Thus, in embodiments where a densely-woven cloth is used, it is preferred that the densely-woven cloth, when stretched around the circumference of a fully-expanded valve, does not permit the hydrogel material to migrate through the cloth and into the internal lumen of the stent 120. In a preferred embodiment in which the adaptive seal 130 is provided on a substrate, the adaptive seal 130 preferably expands only radially outwardly of the heart valve 100.

A hydrogel is generally understood to refer to a polymer or other material that expands or swells in response to an initiating condition, such as changes in temperature, electrical field, magnetic field, chemical environment, pH, and/or phase changes, for example, contact with a liquid. In a preferred embodiment, the adaptive seal does not comprise, or is not, a silicone polymer or other lubricous material. One type of hydrogel is a hydrophilic polymer which physically expands or swells when it contacts and absorbs a liquid, such as water. The extent of the physical expansion or swelling by a hydrophilic polymer is typically limited by the covalent or physical cross-links that oppose the absorption of water once the hydrogel reaches an equilibrium swelling state. Thus, the extent of expansion may be designed or tuned to preferred dimensions based on chemically modifying these crosslinkages. Hydrophilic polymers are highly absorbent and possess a degree of flexibility that is very similar to natural tissue due to their substantial water content.

Examples of hydrophilic polymers, e.g., hydrogels, include, but are not limited to, poly(ethylene oxide), poly(hydroxyethyl methacrylate), poly(vinyl alcohol), polyacrylamide, poly(vinylpyrrolidone), poly(ethyloxazoline), poly(propylene oxide), poly(ethylene glycol)poloxamines, polyacrylamide, hydroxypropylmethacrylate (HPMA), poly(ethylene glycol), polymethacrylate, poly(methyl methacrylate) polylactic acid, carboxymethyl cellulose, hydroxyethyl cellulose, methylhydroxypropyl cellulose, polysucrose, hyaluronate, chondroitin sulfate, dextran, alginate, chitosan, gelatin, and derivatives, mixtures, and copolymers thereof.

Hydrogels can be sensitive to stimuli and respond to changes in the surrounding environment, e.g., an initiating condition, such as changes in temperature, electrical field, magnetic field, chemical environment, pH, and/or phase changes, for example, contact with a liquid. The hydrogels contemplated for use in connection with bioprosthetic heart valves, as described herein, are initially provided in the contracted state and expand or swell only after exposure to an initiating condition. The rate and extent of swelling of the hydrogel can be configured by chemically modifying the hydrogel. For example, where it is desired to control or delay the start or the rate of swelling or expansion of the hydrogel upon exposure to the initiating condition, the hydrogel can be crosslinked with cross-linkers that degrade in response to being exposed to the same or a different initiating condition that causes the hydrogel to expand or swell.

Thus, in a preferred embodiment the rate and extent of expansion of the hydrogel is controlled and fine-tuned by chemically modifying the hydrogel or by incorporating degradable cross-linkers. In a preferred embodiment, the adaptive seal is or comprises a delayed-swelling hydrogel which will not expand for a period of time after exposure to an initiating condition. This period of time is preferably at least 1 minute, more preferably at least 2 minutes, and most preferably at least 5 minutes. The delayed-swelling hydrogel can be produced by incorporating biodegradable cross-linkers in the hydrogel polymer to generate a delayed swelling hydrogel. Once the hydrogel is exposed to an initiating condition, the biodegradable cross-linkers can degrade at a desired rate to permit swelling at a corresponding rate after an initial exposure to the initiating condition. The cross-linkers can be selected to slowly degrade upon exposure to a physiological fluid, such as blood. As the cross-linkers degrade, the hydrogel will expand and swell.

While the rate of hydrogel expansion can be controlled, it is understood that the hydrogel preferably reaches its full expansion, e.g., an equilibrium state, within a period of time to permit the implanting physician to confirm the absence of PVL of the implanted heart valve. In a preferred embodiment, the adaptive seal reaches its full expansion within 5 hours of implantation, preferably within 1 hour of implantation, and most preferably within 15 minutes of implantation. Thus, the biodegradable cross-linkers of the hydrogel are preferably completely degraded or severed within 5 hours, preferably within 1 hour, and most preferably within 15 minutes of exposure to the initiating condition.

Figure 3A:
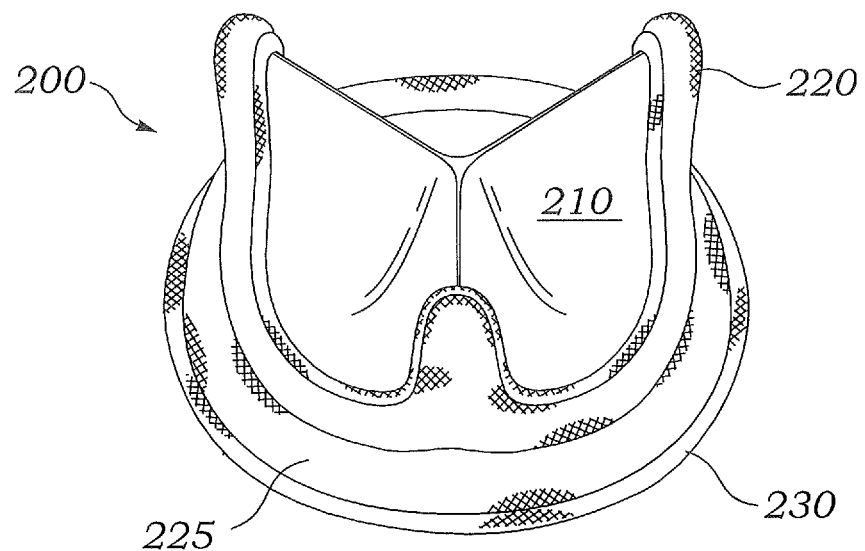
FIG. 3A is a perspective view of the outflow portion of another embodiment of a bioprosthetic heart valve with the adaptive seal located about the periphery of the sewing ring.
Figure 3B:
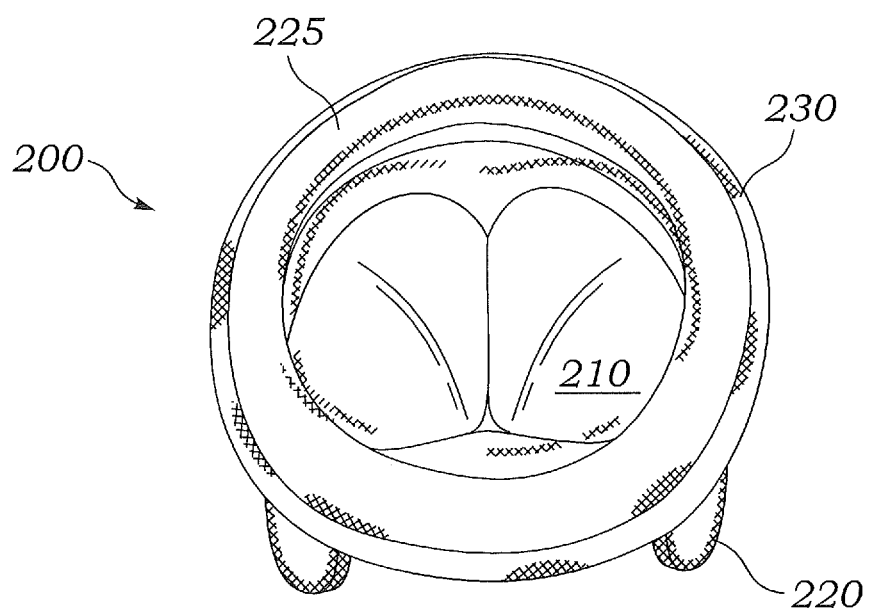
FIG. 3B is a perspective view of the inflow portion of the bioprosthetic heart valve of FIG. 3A.

FIGS. 3A and 3B depict a surgical heart valve 200 comprising a biological tissue leaflet structure 210 comprising three flexible leaflets and a frame 220 comprising three commissure posts. A sewing ring 225 defines the inflow portion of the valve 200 and is used to attach the valve 200 to the valve annulus. The sewing ring 225 can be circular or scalloped. The sewing ring 225 defines a suture-permeable cuff made of an inner body of silicone covered with a permeable or semi-permeable material or fabric.

In the embodiment depicted in FIGS. 3A and 3B, the adaptive seal 230 is preferably a hydrogel which is exposed and coupled externally about the circumferential edge of the sewing ring 225 to provide conforming engagement between the sewing ring 225 and the inner surface of the annulus where the valve is implanted (not shown). The adaptive seal 230 can also be provided inside the sewing ring 225, with a permeable or semi-permeable fabric covering being made of a material having sufficient elasticity to permit swelling and expansion of the adaptive seal 230 within the sewing ring 225. Alternatively, the adaptive seal 230 can also be provided as a hydrogel coating on the sewing ring 225 as a result of dipping the material or fabric constituting the sewing ring into a hydrogel solution. In the embodiment depicted in FIGS. 3A and 3B, the adaptive seal 230 comprises a hydrogel material that is disposed on a wire that is wrapped around the sewing ring 225 and preferably secured onto the sewing ring by adhesives or by sutures. Because the valve 200 is surgically implanted and does not require the valve 200 to be crimped or collapsed, the substrate for the hydrogel material is not required to be expandable or elastic.

Figure 4A:
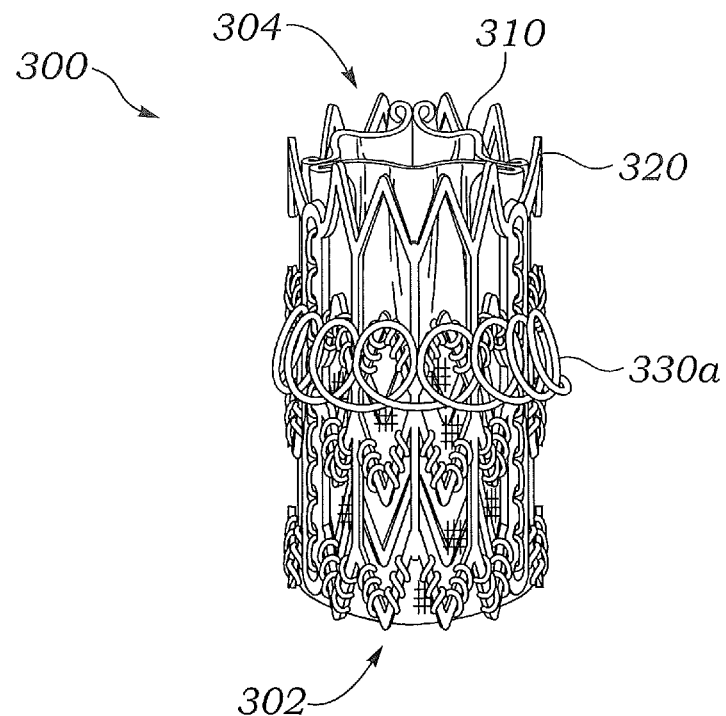
FIGS. 4A-4B are perspective views of an embodiment of a bioprosthetic heart valve in a collapsed and an expanded state, respectively.
Figure 4B:
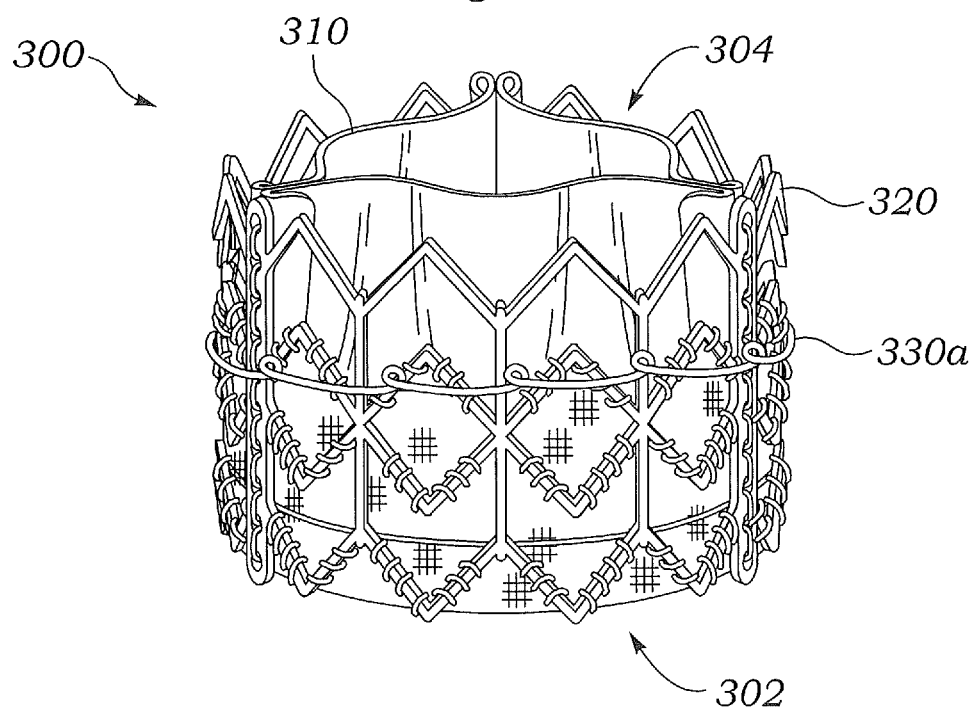

FIGS. 4A and 4B depict an embodiment of a transcatheter heart valve 300 which comprises an adaptive seal 330a of a different configuration from the one depicted in FIGS. 1-2. The heart valve 300 comprises a biological tissue leaflet 310 attached to a stent 320. The heart valve 300 is further depicted as comprising a hydrogel-coated wire 330a surrounding the periphery of the stent 320. The hydrogel-coated wire 330a, by virtue of its geometry, comprising a plurality of loops, will permit expansion of the heart valve 300 for implantation. One or more hydro-gel coated wires can be used on the valve.

The hydrogel-coated wire 330a is formed as a plurality of loops. When the heart valve 300 is in its compressed or unexpanded configuration, as depicted in FIG. 4A, the hydrogel-coated wire 330a comprises a plurality of larger loops. When the heart valve 300 is in its expanded configuration, as depicted in FIG. 4B, the loops reduce in size significantly. The presence of the loops provides a degree of flexibility for radial expansion of the heart valve 300.

Suitable hydrogel-coated wires include Azur Peripheral HYDROCOIL® (MicroVention Terumo, Inc., Aliso Viejo, Calif.), which is a platinum coil with an expandable poly(acrylamide-co-acrylic acid) hydrogel and overcoiled with a stretched platinum coil. An advantage of using the hydrogel-coated wire 330a is that it stays substantially close to the stent 320 in both the expanded and the compressed states such that it does not significantly add material bulk. This permits the fabrication of transcatheter heart valves having substantially narrower delivery profiles than would be expected when such valves include a PVL skirt, for example.

In a preferred embodiment, at least one end of the hydrogel-coated wires is attached to the stent 320 by crimping. In another preferred embodiment, the hydrogel-coated wires are crimped in one, two, three, or four locations along the stent 320. As depicted in FIGS. 4A and 4B, the hydrogel-coated wire 330a is positioned around the entire circumference of the heart valve at a distance from both the inflow end 302 and the outflow end 304. In a preferred embodiment, the hydrogel-coated wire 330a undergoes limited expansion within the first 3 minutes, and fully expands within 20 minutes.

While FIGS. 4A and 4B depict the adaptive seal 330a taking the form of a hydrogel-coated wire, it is understood that the adaptive seal 330a can also be provided as a hydrogel coating on the stent 320. In accordance with one aspect of this embodiment, the stent 320 can be dipped in or spray coated with a hydrogel solution and allowed to dry prior to assembling the stent 320 with the tissue leaflet 310.

Figure 4C:
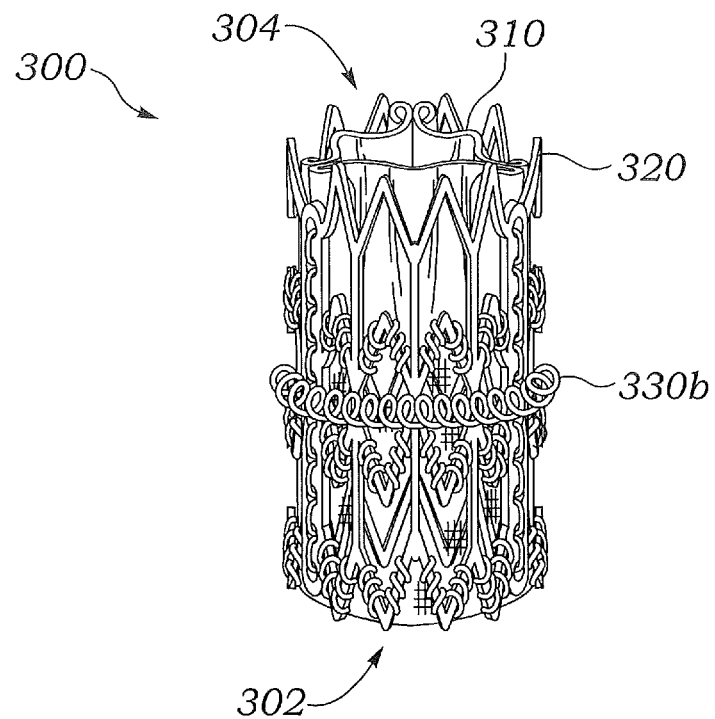
FIGS. 4C-4D are perspective views of another embodiment of a bioprosthetic heart valve in a collapsed and an expanded state, respectively.
Figure 4D:
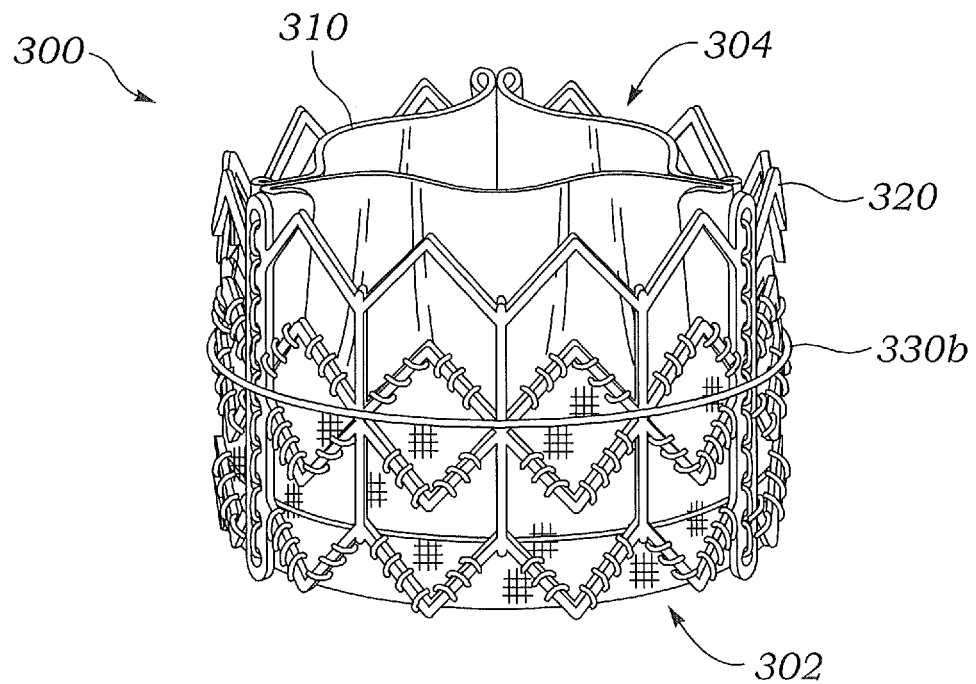

FIGS. 4C and 4D depict the heart valve 300 in which the hydrogel-coated wire 330b is provided in two different configurations. When the valve 300 is in a compressed state, as depicted in FIG. 4C, the hydrogel-coated wire 330b is provided in a first configuration, in which the hydrogel-coated wire 330b is tightly coiled. When the valve is in an expanded state, as depicted in FIG. 4D, the hydrogel-coated wire 330b is provided in a second configuration, in which the hydrogel-coated wire 330b is substantially straight. The hydrogel-coated wire 330b can comprise a shape memory metal, such as Nitinol, such that it takes on the substantially straight configuration upon being heated to a particular temperature, preferably in the range of about 24-37° C. The temperature at which a shape memory metal, such as Nitinol, will change configurations can be fine-tuned by altering the profile of the shape memory metal. Alternatively, the hydrogel-coated wire 330b can be a non-metal wire that is elastically stretchable between the first and second configurations. It is understood that where an elastic wire is used, the elastic wire does not cause significant compression of the stent 320 in an expanded state.

Figure 4E:
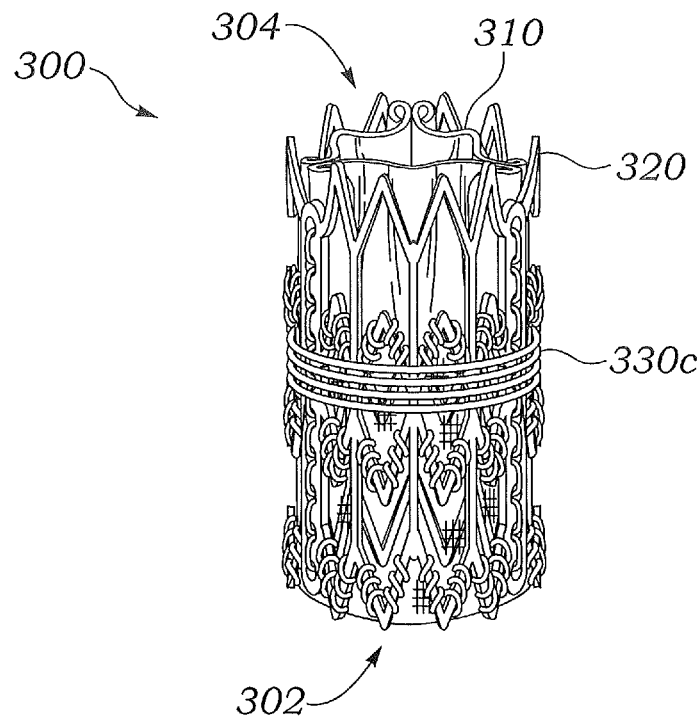
FIGS. 4E-4F are perspective views of a further embodiment of a bioprosthetic heart valve in a collapsed and an expanded state, respectively.
Figure 4F:
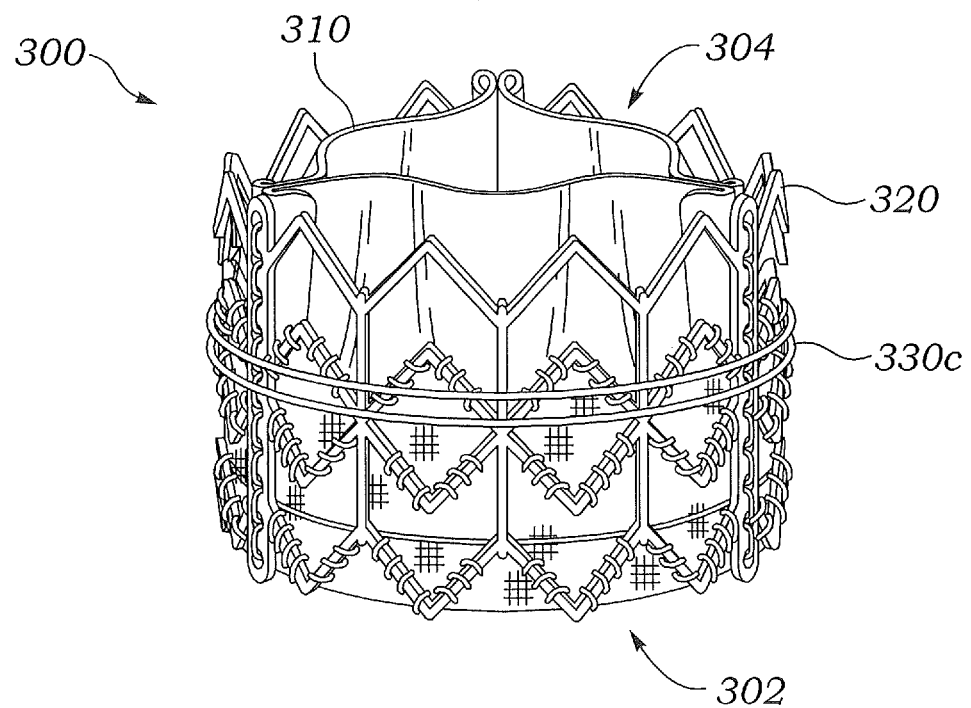

FIGS. 4E and 4F depict the heart valve 300 in which the hydrogel-coated wire 330c is provided as a straight wire that encircles or is coiled around the outer external periphery of the heart valve 300. In the preferred embodiment depicted in FIGS. 4E and 4F, the hydrogel-coated wire 330c has a length that permits it to be coiled around the entire outer circumference of the compressed valve (FIG. 4E) more than once. Preferably, only one end of the hydrogel-coated wire 330c is affixed to the stent 320 by crimping. The other free end of the hydrogel-coated wire 330c is permitted to move in relation to the valve 300 as it is expanded to the fully-expanded state (FIG. 4F). In a preferred embodiment, the hydrogel-coated wire 330c has a length that permits it to be coiled around the heart valve in its fully-expanded state at least once, if not twice. One advantage provided by the hydrogel-coated wire 330c in FIGS. 4E-4F is that it will add, to a lesser event, to the delivery profile of the compressed heart valve 300.

Figure 5A:
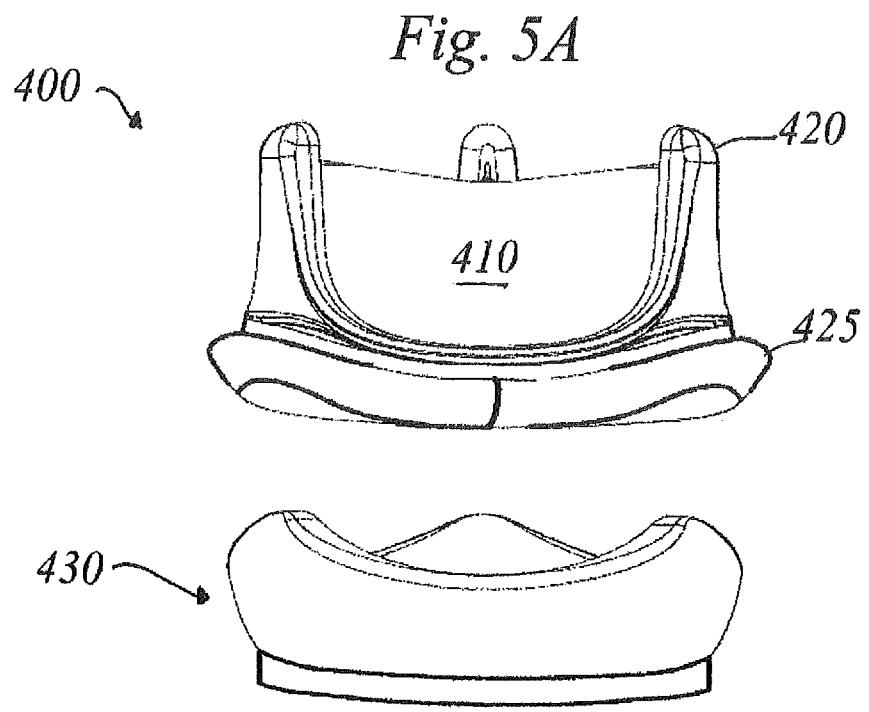
FIG. 5A is an exploded perspective view of a further embodiment of a bioprosthetic heart valve showing the tissue valve portion and the stented sealing cloth.
Figure 5B:
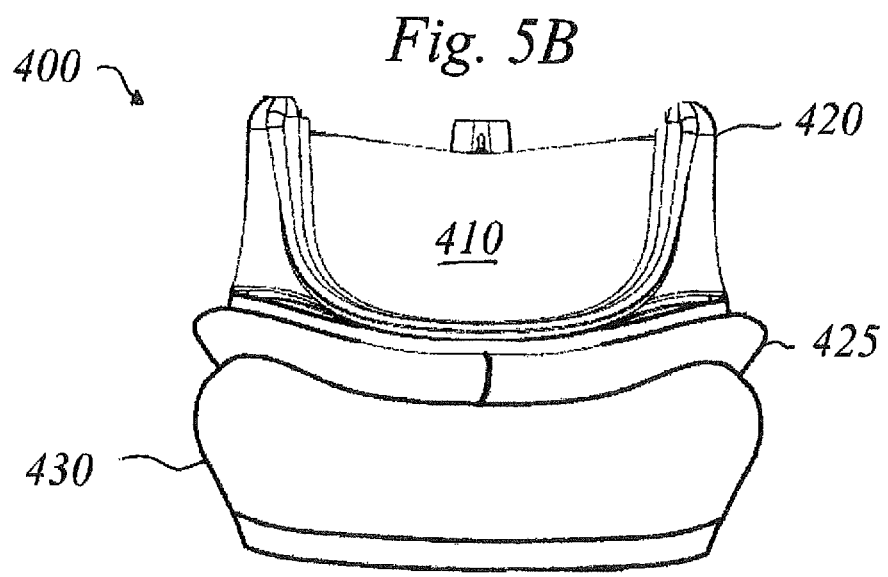
FIG. 5B is a perspective view of the bioprosthetic heart valve of FIG. 5A in which the tissue valve portion and the stented sealing cloth are assembled together.

FIGS. 5A and 5B depict an embodiment of a replacement heart valve 400 which can be implanted using minimally-invasive techniques. The heart valve 400 comprises a biological tissue 410 coupled to a supporting frame 420 comprising three commissure posts, a sewing ring 425 and a frame stent 430 comprising a cloth covered anchoring frame. The frame stent 430 can be balloon expanded after implantation and is characterized as providing a greater area of engagement between the heart valve 400 and the arterial or cardiac walls. The frame stent 430 therefore is believed to reduce the incidence of PVL of the implanted heart valve 400. In a preferred embodiment, the frame stent 430 or the cloth material constituting the frame stent 430 can be coated with the adaptive seal or hydrogel material. In another preferred embodiment, the adaptive seal or hydrogel material can be contained within the cloth material of the frame stent 430.

One advantage afforded by the replacement heart valve 400 is that the manufacturing of the valve portion consisting of the biological tissue 410, the supporting frame 420 and the sewing ring 425 can be done separately from the manufacture of the cloth-covered frame stent 430 to constitute the adaptive seal. In the embodiment depicted in FIGS. 5A and 5B, the cloth covered frame stent 430 is dipped in or sprayed with a hydrogel solution prior to assembly with the valve portion. Alternatively, the hydrogel material can be provided within the cloth covered frame stent 430, provided that the cloth is sufficiently elastic to permit expansion by the hydrogel material contained therein. Once the valve portion and the frame stent 430 are separately prepared, the two can be assembled together.

FIGS. 6A-6C depict an expandable bioprosthetic heart valve 600 and its delivery system 602 in the various stages from a collapsed delivery configuration with the adaptive seal 610 being adjacent the delivery system, as depicted in FIG. 6A, an intermediate configuration with the adaptive seal 610 is positioned around the bioprosthetic heart valve 600, as depicted in FIG. 6B, and an expanded configuration, in which the heart valve 600 is fully expanded and the adaptive seal 610 being disposed around the heart valve 600, as depicted in FIG. 6C. In a preferred embodiment, the adaptive seal 610 depicted in FIGS. 6A through 6C is a hydrogel-coated wire.

Expandable bioprosthetic heart valves are known in the art and the illustrated heart valve 600 illustrated in FIGS. 6A through 6C is representative of a number of such valves which can be converted from a narrow constructed configuration to a wider expanded configuration. Typically, the valves are balloon expanded into position at a target annulus after having been advanced through the vasculature, although self-expanding valves are also known. The most common delivery routes commence at the femoral or carotid arteries, though other more direct routes through chest ports are also known. One such expandable prosthetic heart valve is the Edwards SAPIEN® or SAPIEN XT® Transcatheter Heart Valve available from Edwards Lifesciences of Irvine, Calif. The Edwards SAPIEN® valve can be placed either through a transfemoral or transapical approach.

The delivery system 602 includes an elongated catheter 604 having an expansion balloon 646 near a distal end thereof. The bioprosthetic heart valve 600 mounts around the balloon 646 and is expanded thereby. The system further includes proximal connectors 608 for delivery of balloon inflation fluid, passage of a guide wire, or other such functions. In the exemplary embodiment, the bioprosthetic heart valve 600 includes a plurality of balloon expandable struts in between three axially-oriented commissure bars 605. Bioprosthetic tissue mounts within the framework created by the struts and bars 605, such as with supplementary fabric.

In most cases, it is desirable to reduce the delivery profile of the collapsed delivery configuration as depicted in FIG.

6A. One way of achieving a reduced delivery profile is to provide the adaptive seal 610 such that it does not initially encircle or wrap the collapsed bioprosthetic heart valve 600 but instead is allowed to trail along the elongated catheter in a first delivery configuration. In a preferred embodiment, the collapsed delivery configuration depicted in FIG. 6A is provided within a sheath (not shown). Reducing the delivery profile of the collapsed delivery configuration will permit a reduced French size for the corresponding sheath.

As the delivery system is inserted into the vasculature of the patient's body, both the bioprosthetic heart valve 600 and the adaptive seal 610 will be exposed to blood and other bodily fluids. As explained above, it is undesirable for the adaptive seal 610 to swell or expand substantially, if at all, immediately upon exposure to blood because such expansion will interfere with the ability to deliver the bioprosthetic heart valve 600 through the patient's vasculature and to advance the valve 600 out of the delivery sheath. Thus, in a preferred embodiment, the adaptive seal 610 is chemically tuned such that it will respond to one or a plurality of initiating conditions, such as, for example, exposure to liquid and an additional condition, such as pH, temperature, a change in the electrical or magnetic field, or a change in the chemical environment, after a predetermined period of time of such exposure. In another embodiment, the adaptive seal 610 will include a biodegradable cross-linker which degrades at a predetermined rate upon exposure to an initiating condition.

Once the bioprosthetic heart valve 600 is delivered proximate to the intended site of implantation, the sheath is removed. Upon removal of the sheath and before significant expansion of the heart valve 600, the adaptive seal 610 coils or wraps around the external periphery of the heart valve 600 in a second configuration. The adaptive seal 610 can be comprised of a hydrogel material disposed on either a shape memory metal or other material that is configured to elastically wrap around the heart valve 600 once it is exposed from the sheath. In a preferred embodiment, the length of the adaptive seal 610 is longer than the circumference of the fully-expanded valve 600 such that a portion of the adaptive seal 610 overlaps. In this manner, gaps between the two ends of the adaptive seal 610 can be avoided.

As indicated above, the adaptive seal 610 preferably comprises a shape-memory material or metal, such as Nitinol, which is coated with a hydrogel and which is configured to coil around the outer circumference of the valve 600 based reaching or exceeding a transformation temperature. In a preferred embodiment, the transformation temperature is between about 24-25° C., about 25-26° C., about 26-27° C., about 27-28° C., about 28-29° C., about 29-30° C., about 30-31° C., about 31-32° C., about 32-33° C., about 33-34° C., about 34-35° C., about 35-36° C., and about 36-37° C. In embodiments where the valve 600 comprises a self-expanding stent made of shape-memory material or metal, the transformation temperature for the stent is higher than the transformation temperature for the adaptive seal 610 so as to ensure that the adaptive seal 610 coils around the valve 600 before the valve 600 begins to expand or is substantially or fully expanded.

FIG. 6C depicts the bioprosthetic heart valve 600 in a fully-expanded configuration with the adaptive seal 610 being disposed around the circumference of the valve 600. In a particularly preferred embodiment, the adaptive seal 610 does not swell or expand until after it assumes a fully expanded configuration as depicted in FIG. 6C.

FIGS. 7A-7C depict the expandable bioprosthetic heart valve 600 having a hydrogel-coated wire 610a taking on different configurations that similarly permit a smaller delivery profile. The hydrogel-coated wire 610a is provided in a first delivery configuration as a straight wire, as depicted in FIG. 7A. This permits the compressed bioprosthetic heart valve 600 and its delivery system 602 to fit within a sheath having a reduced delivery profile. Once the sheath (not shown) is removed, the hydrogel-coated wire 610a takes on a second configuration, in which it is both coiled and wrapped around the outer periphery of the heart valve 600 at least two times (FIG. 7B), and a third configuration, in which the hydrogel-coated wire 610a remains in a coiled configuration but is wrapped around the outer periphery of the heart valve 600 only once (FIG. 7C).

FIGS. 8A-8C depict the expandable bioprosthetic heart valve 600 having a hydrogel-coated wire 610b taking on another alternate configuration permitting a smaller delivery profile. The hydrogel-coated wire 610b is provided in a first delivery configuration as a straight wire, as depicted in FIG. 8A. This permits the compressed bioprosthetic heart valve 600 and its delivery system 602 to fit within a sheath having a reduced delivery profile. Once the sheath (not shown) is removed, the hydrogel-coated wire 610b takes on a second configuration, in which it is wrapped around the outer periphery of the heart valve 600 (FIGS. 8B and 8C). Again, the length of the hydrogel-coated wire 610b is provided such that it encircles the external periphery of the compressed valve a plurality of times, preferably at least 2, 3, or 4 times (FIG. 8B). As the hydrogel-coated wire 610b is coupled to the stent at only one end, the heart valve 600 is permitted to expand radially in its fully expanded state (FIG. 8C).

With respect to the embodiments depicted in FIGS. 6-8, it is understood that the heart valve 600 can be packaged in a collapsed delivery configuration with the adaptive seal being positioned adjacent the delivery system 602 as depicted in FIG. 6A, 7A or 8A. This allows the heart valve 600 to be provided to the implanting physician in a substantially ready-to-use condition out of the package.

As indicated above, the biological tissues suitable for the heart valves described herein are treated so as to permit storage without a liquid preservative solution, e.g., dry storage. To that end, the biological tissue can be contacted or immersed in a treatment solution comprising a polyhydric alcohol or polyol, preferably a glycerol. The glycerol can be provided in an aqueous, non-aqueous or a substantially non-aqueous solution. In a preferred embodiment, the non-aqueous solution (the solvent is not water) or the substantially non-aqueous solution is an alcoholic solution. In a preferred embodiment, the alcoholic solution comprises one or a combination of lower alcohols, preferably $C_1$-$C_3$ alcohols. The biological tissue following treatment with the treatment solution is dehydrated or substantially dehydrated. In a preferred embodiment, the water content of the biological tissue following treatment with the treatment solution is reduced at least about 10%, preferably at least about 25%, preferably at least about 50%, preferably at least about 75%, preferably at least about 80%, and preferably at least about 90%.

The time of contact between the biological tissue and the treatment solution depends on the thickness and type of tissue. Once the biological tissue has been sufficiently exposed to the treatment solution, the tissue is removed from the solution and exposed to ambient air or an inert environment (e.g., nitrogen), at standard room temperature and humidity so as not to adversely affect tissue properties. Preferably, the drying is performed in a clean room or in a laminar flow bench at ambient room conditions for about 1 to 4 hours. In a preferred embodiment, the treatment solution is a solution of glycerol and a $C_1$-$C_3$ alcohol, wherein the treatment solution comprises about 60-95% by volume glycerol. Suitable treatment for the biological tissues are described in U.S. Pat. No. 8,007,992, issued Aug. 30, 2011, to Edwards Lifesciences Corp., the entire contents of which are incorporated herein by reference as if fully set forth herein. In another preferred embodiment, the tissue can be treated as described in U.S. Pat. No. 6,534,004, issued Mar. 18, 2003, issued to The Cleveland Clinic Foundation, the entire contents of which are incorporated herein by reference in its entirety as if fully set forth herein.

In a preferred embodiment, the adaptive seal is made of a material that expands after exposure to one or more initiating conditions. The adaptive seal is preferably a hydrophilic polymer or a hydrogel-coated wire that is made up of a hydrogel material that expands or swells when exposed to an aqueous liquid, such as saline or blood. Preferably, the hydrogel material does not fully expand or swell until after a period of contact with the initiating condition (e.g., fluid), which provides physicians the ability to deliver and control the implantation of the device at the desired location. This can be accomplished by utilizing hydrogels or hydrogel-coated wires in which the hydrogel material has been cross-linked with a degradable cross-linker. Thus, the substantial expansion of the adaptive seal takes place after initial contact with the initiating condition. Alternatively, the seal can be made of a hydrogel that initially expands slowly and then expands more rapidly after a period of time has elapsed from exposure to the initiating condition. In a preferred embodiment, the rapid expansion of the adaptive seal occurs about 30 seconds, about 60 seconds, about 2 minutes, or about 5 minutes after exposure to the initiating condition. In embodiments where the initiating condition is exposure to fluid, preferably an aqueous fluid such as blood, the adaptive seal is provided in a substantially dehydrated state.

The adaptive seal described herein can be provided in the form of a cloth, a film, a coating, a foam, or a hydrogel-coated wire and comprise an expandable material that impregnates a suitable substrate, is chemically coupled to a suitable substrate, or is contained within a permeable or semi-permeable barrier that permits the entry of fluid but contains the expandable material. The expandable material is preferably a hydrogel or an organic polymer that is cross-linked via covalent, ionic or hydrogen bonds to create a three-dimensional open lattice structure which entraps water molecules to form a gel. Alternatively, the adaptive seal is a hydrogel-coated wire, such as HYDROCOIL® (MicroVention Terumo, Inc., Aliso Viejo, Calif.), which is a platinum coil with an expandable poly(acrylamide-co-acrylic acid) hydrogel and overcoiled with a stretched platinum coil. When positioned in situ, the adaptive seal expands from its reduced radial profile to an increased radial profile. U.S. Patent Application Publication No. 2013/0190857, published Jul. 25, 2013, to Endoluminal Sciences Pty. Ltd. is incorporated herein by reference in its entirety.

The bioprosthetic heart valve and adaptive seal can preferably be packaged in double sterile barrier packaging consisting of a rigid tray (PETG) with a TYVEK® non-woven polyolefin lid. The package is sealed in a cleanroom and sterilized in 100% ethylene oxide. Suitable packaging systems for the bioprosthetic heart valves disclosed herein are described in U.S. Patent Application Publication No. 2011/0214398, published Sep. 8, 2011, to Edwards Lifesciences Corp., and is incorporated herein by reference in its entirety. In embodiments where the bioprosthetic heart valve is provided along with a delivery device, suitable packaging systems are described in U.S. Patent Application Publication No. 2013/0152659, published Jun. 20, 2013; U.S. Patent Application Publication No. 2012/0158128, Jun. 21, 2012, and U.S. Patent Application Publication No. 2012/0239142, published Sep. 20, 2012, all to Edwards Lifesciences Corp, and all incorporated by reference herein in their entireties.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A bioprosthetic heart valve, comprising:
   a dry biological tissue leaflet structure comprising an inflow portion and an outflow portion;
   an expandable supporting frame coupled to the dry biological tissue leaflet structure; and
   an adaptive seal coupled to the expandable supporting frame, the adaptive seal comprising an expandable material configured to expand after exposure to an initiating condition;
   wherein the expandable material is a substantially dehydrated hydrogel that has been crosslinked with a biodegradable crosslinker;
   wherein the dry biological tissue leaflet structure, the expandable supporting frame, and the adaptive seal are configured for joint storage in a sealed package that does not contain a liquid storage solution.

2. The bioprosthetic heart valve of claim 1, wherein the adaptive seal surrounds a periphery of the expandable supporting frame, and is coupled thereto at a spaced distance from the inflow portion and the outflow portion of the dry biological tissue leaflet structure.

3. The bioprosthetic heart valve of claim 1, wherein the expandable material is configured to expand in an outward radial direction away from the dry biological tissue leaflet structure.

4. The bioprosthetic heart valve of claim 1, wherein the expandable material is configured to expand in a longitudinal direction toward the inflow portion and the outflow portion of the dry bioprosthetic tissue leaflet structure.

5. The bioprosthetic heart valve of claim 1, wherein the expandable material is configured to expand in both an outward radial direction and a longitudinal direction relative to the dry biological tissue leaflet structure.

6. The bioprosthetic heart valve of claim 1, wherein the initiating condition is selected from: a change in temperature, a change in an electrical field, a change in a magnetic field, a change in a chemical environment, a change in pH, contact with a liquid, and combinations thereof.

7. The bioprosthetic heart valve of claim 1, wherein the adaptive seal further comprises a substrate, and wherein the expandable material is disposed on one or more portions of the substrate.

8. The bioprosthetic heart valve of claim 7, wherein the substrate is located between the expandable material and the expandable supporting frame.

9. The bioprosthetic heart valve of claim 7, wherein the substrate is configured to prevent expansion of the expandable material in an inward radial direction toward the dry biological tissue leaflet structure.

10. The bioprosthetic heart valve of claim 7, wherein the substrate is configured to radially expand upon expansion of the expandable supporting frame.

11. The bioprosthetic heart valve of claim 1, wherein the expandable supporting frame is a stent comprising a plurality of struts and open cells.

12. The bioprosthetic heart valve of claim 11, wherein the adaptive seal further comprises one or more discrete patches disposed within the open cells of the stent, wherein each of the one or more discrete patches comprises the expandable material.

13. The bioprosthetic heart valve of claim 1, wherein one or more portions of the expandable supporting frame are coated with the expandable material.

14. A sealed package comprising the bioprosthetic heart valve of claim 1, wherein the sealed package does not contain a liquid storage solution.

* * * * *